US00PP11422P

United States Patent [19]

Austin

[11] Patent Number: Plant 11,422

[45] Date of Patent: Jun. 20, 2000

[54] SHRUB ROSE PLANT NAMED 'AUSLOT'

[75] Inventor: David C. H. Austin, Albrighton, United Kingdom

[73] Assignee: David Austin Roses Limited, Wolverhampton, United Kingdom

[21] Appl. No.: 09/168,198

[22] Filed: Oct. 7, 1998

[51] Int. Cl.[7] ..... A01H 5/00

[52] U.S. Cl. ..... Plt./102

[58] Field of Search ..... Plt./102, 107, 108, Plt./141, 149, 150

*Primary Examiner*—Howard J. Locker

*Attorney, Agent, or Firm*—Klarquist Sparkman Campbell Leigh & Whinston, LLP

[57] ABSTRACT

A shrub rose plant having disease resistance; repeat flowering, old-fashioned shaped red-purple flower; and a strong growing plant with a bushy habit.

1 Drawing Sheet

The present invention relates to a new and distinct variety of shrub rose plant of the *Rosa hybrida* class which was originated by me by crossing the variety 'Prospero', unpatented, with an unnamed seedling.

The primary objective of this breeding was to produce a new shrub rose variety having good disease resistance, repeat flowering of old-fashioned shaped red flowers on a strong growing plant with a bushy habit. The objective was substantially achieved, along with other desirable improvements, as evidenced by the following unique combination of characteristics that are outstanding in the new variety and that distinguish it from its parents, as well as from all other varieties of which I am aware:

1. Bushy habit;
2. Strong growth; and
3. Large, dome-shaped, red-purple flowers.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Prospero' (unpatented).

*Pollen parent.*—Unnamed seedling of unknown parentage.

Classification:

*Botanical.*—*Rosa hybrida.*

*Commercial.*—Shrub.

FLOWER

Observations made from specimens grown in a garden environment at Albrighton, Wolverhampton, England, July, 1996.

Blooming habit: Recurrent.

Bud:

*Size.*—About one inch long when the petals start to unfurl.

*Form.*—The bud form is short, pointed ovoid.

*Color.*—When sepals first divide, bud color is Red Group 53D and Red Group 53C. When half blown, the upper sides of the petals are Red-Purple Group 66A and Red-Purple Group 61C, and the lower sides of the petals are Red-Purple Group 63B.

*Sepals.*—Color: Yellow-Green Group 144B. Surface texture: Upper side hairy; under side slightly prickly and waxy. There are three normally appendaged sepals and two unappendaged sepals with hairy edges. There is a Greyed-Red Group 181A stripe down through center of sepal.

*Receptacle.*—Color: Yellow-Green Group 144B. Shape: Funnel. Size: Medium (about ⅜ to ⅜ inch long×⅜ to ⅜ inch wide). Surface: Smooth, very slightly hairy.

*Peduncle.*—Length: Medium, averaging about 1 to 1½ inches. Surface: Smooth, prickly. Color: Greyed-Red Group 182A and Yellow-Green 144B. Strength: Erect.

Bloom:

*Size.*—Large to medium. Average open size is 3½ to 4 inches.

*Borne.*—Singly and several together in pyramidal clusters of two to three blooms.

*Stems.*—Normal strength. Average length is about 8 to 24 inches.

*Form.*—When first open: Bloom is cupped. Permanence: Outer petals curl back.

*Petalage.*—Number of petals under normal conditions: 82.

*Color.*—The upper sides of the petals are Red-Purple Group 57A and Red-Purple Group 57C. The reverse sides of the petals are Red-Purple Group 64C and Red-Purple Group 67C. The base of each petal is Yellow Group 3C. The major color on the upper sides is Red-Purple Group 57A.

*Variegations.*—None.

*Discoloration.*—The general tonality at the end of the first day: Red-Purple Group 57A. At the end of the third day: Same.

*Fragrance.*—Moderate, light tea character.

Petals:

*Texture.*—Leathery.

*Shape.*—Oval.

*Form.*—Tips slightly recurved on outer petals. Moderately quilled on central petals.

*Arrangement.*—Irregular. Petaloids are few and small in the center.

*Persistence.*—Petals hang on and dry.

*Lastingness.*—On the plant: Long, about 5 days. As a cut flower: Not tested.

Reproductive parts:

*Anthers.*—Size: Medium. Quantity: Many Color: Yellow Group 8A. Arrangement: Partly tucked in calyx.

*Filaments.*—Color: Yellow Group 10A.

*Pollen.*—Color: Yellow-Orange Group 15A.

*Styles.*—Color: Yellow-Green Group 149D.

*Stigmas.*—Color: Yellow-Orange Group 23B.

Form: Shrub.

Growth: Vigorous, bushy. Mature plant is 3½ feet in height and three feet in width.

Foliage: Number of leaflets on normal mid-stem leaves: five to seven.

*Size.*—Medium (5–7" long×4–6" wide).

*Quantity.*—Normal.

*Color.*—New foliage: Upper side: Yellow-Green Group 144A. Lower side: Yellow-Green Group 146C. Old foliage: Upper side: Green Group 137A. Lower side: Yellow-Green Group 146B.

Leaflets:

*Shape.*—Oval.

*Texture.*—Upper side: Leathery, semi-glossy.

*Edge.*—Serrated.

*Serration.*—Single, small.

*Petiole rachis.*—Color: Yellow-Green Group 144B.

*Petiole underside.*—Smooth, with prickles.

*Stipules.*—Medium, about ¾ inch long.

*Disease resistance.*—Resistant to mildew, blackspot and rust under normal growing conditions at Albrighton, Wolverhampton, England.

Wood:

*New wood.*—Color: Greyed-Purple Group 183B. Bark: Smooth.

*Old wood.*—Color: Yellow-Green Group 144B and 143B. From mid-stem upwards: Slight Greyed-Purple 184B. Bark: Smooth.

Prickles:

*Quantity.*—On main canes from base: Ordinary. On laterals from main canes: Ordinary.

*Position.*—Mainly just underneath where the leaflet joins the stem.

*Form.*—Medium to short, hooked downward.

*Color when young.*—Greyed-Purple Group 185A. Yellow-Green Group 144B at tip.

*Color when mature.*—Greyed-Orange Group 165B.

Small prickles:

*Quantity.*—On main stalks: Few. On laterals: Many.

*Color.*—Greyed-Orange Group 165A (lighter).

I claim:

1. A new and distinct variety of shrub rose plant of the *Rosa hybrida* class, substantially as herein shown and described, characterized particularly as to novelty by the unique combination of its disease resistance; repeat flowering, old-fashioned shaped red-purple flower; and a strong growing plant with a bushy habit.

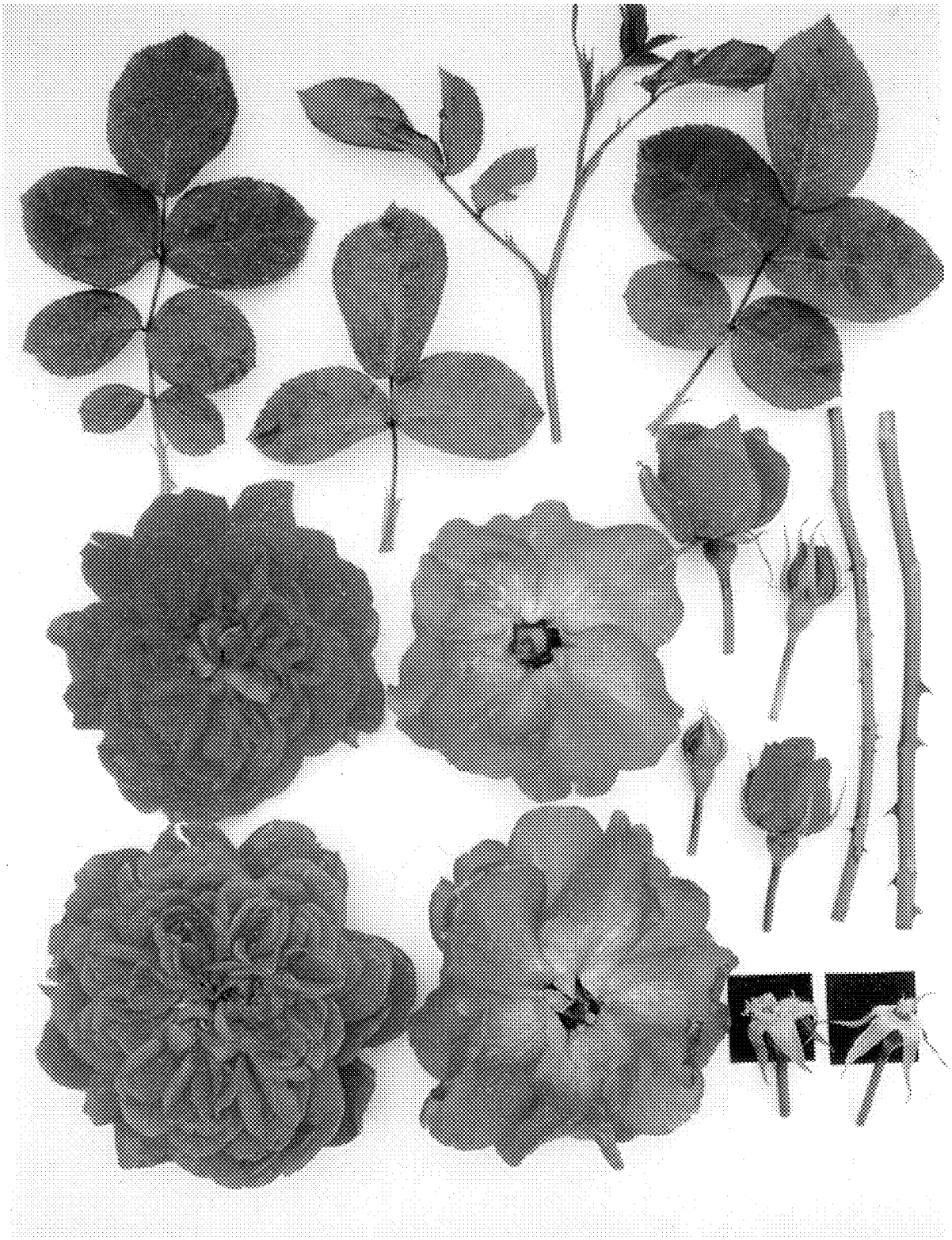

* * * * *